United States Patent [19]

O'Connor

[11] Patent Number: 5,450,860
[45] Date of Patent: Sep. 19, 1995

[54] DEVICE FOR TISSUE REPAIR AND METHOD FOR EMPLOYING SAME

[75] Inventor: Michael T. O'Connor, Flagstaff, Ariz.

[73] Assignee: W. L. Gore & Associates, Inc., Newark, Del.

[21] Appl. No.: 114,711

[22] Filed: Aug. 31, 1993

[51] Int. Cl.⁶ .............................. A61B 17/04
[52] U.S. Cl. ..................... 128/898; 606/224
[58] Field of Search ............... 606/222–226, 606/230, 231; 623/1, 3, 13; 128/898, 654, 660.07

[56] References Cited

U.S. PATENT DOCUMENTS

| | | |
|---|---|---|
| 3,953,566 | 4/1976 | Gore . |
| 4,369,769 | 1/1983 | Edwards .................. 606/61 |
| 4,792,336 | 12/1988 | Hlavacek et al. ........... 623/13 |

OTHER PUBLICATIONS

Article: "Mitral Valve Annuloplasty: The Effect of the Type on Left Ventricular Function"; Tirone E. David, MD et al. 1989.
Article: "Preoperative Evaluation and Surgical Treatment for Tricuspid Regurgitation Associates with Acquired Valvular Heart Disease"; Isao Yada, MD PhD et al., 1990, pp. 771-777.
Article: "Carpentier's Annulus and De Vega's Annuloplasty"; Pierre Grondin, et al. Nov. 1975, pp. 852-861.
Article: "The New De Vega Technique In Tricuspid Annuloplasty"; Gregorio Rabago, MD, et al., pp. 231-238.
Article: "Carpentier's Flexible Ring Versus De Vega's Annuloplasty"; R. Rivera, MD, et al., Feb. 1985, pp. 196-203.
Article: "Surgery For Tricuspid Insufficiency: Long Term Follow-Up After De Vega Annuloplasty"; K. Hopler et al; Sep. 9, 1992.
Article: "Results of Mitral Valvuloplasty with A Suture Plication Technique"; D. F. Shore MD et al; 1980; pp; 349-357.
Article: "Mitral Valvuloplasty: A Learning Curve"; Manuel J. Antunes MD, et al; 1983; pp. II-70-II-75.
Article: "New Surgical Approach to Tricuspid Annuloplasty: Possibility of An Extracardial Suture Technique 'AV-Gathering'"; M. Hoshino et al; Apr. 30, 1991; pp. 263-267.
Article: "Surgical Management of Acquired Tricuspid Valve Disease"; A. Carpentier, et al; Jan. 1974; pp. 53-65.
A Surgical Rounds Patient Education Chart: "Mitral Valve Prolapse"; Illust. Jean Miller; Date Unknown.
Article: "A 'Designer' Annuloplasty Ring For Patients with Massive Mitral Annular Dilatation"; Sara Shumway et al; Dec. 1988; pp. 695-696.
Article: "Conservative Repair of Mitral and Tricuspid Valves"; Raul Garcia-Rinaldi, MD, et al; Date Unknown.
Article: "Techniques In Cardiac Surgery"; Denton A. Cooley, MD 1984.

(List continued on next page.)

Primary Examiner—Gary Jackson
Attorney, Agent, or Firm—David J. Johns

[57] ABSTRACT

The present invention comprises an improved device and method for plicating tissue. The apparatus of the present invention employs a ligament of expanded polytetrafluoroethylene or similar material which is of sufficient width to allow it to be retained in place by sewing through it using conventional sutures. The present invention is particularly applicable to the repair of heart valves where it can be relatively rapidly installed around a weakened heart valve yet is not susceptible to "guitar string" pull-out or similar problems.

14 Claims, 7 Drawing Sheets

OTHER PUBLICATIONS

Literature: Baxter Edwards; Carpenter-Edwards® Annuloplasty Rings; Nov. 1990.

Article: "Technique and Results of Tricuspid Annuloplasty"; Gregorio Rabago, MD et al. 1986; pp. 247–253.

Article: "De Vega's Semicircular Annuloplasty For Tricuspid Valve Regurgitation"; Jeng Wei MD, et al; Jun. 2, 1992 pp. 482–485.

Article: "Carpentier's Flexible Ring Versus De Vega's Annuloplasty: A Prospective Randomized Study"; R. Rivera et al; Feb. 1985; pp. 233–234.

Article: "Direct Imaging of the Tricuspid Valve Annular Motions By Fiberoptic Cardioscopy in Dogs"; Naoki Minato MD et al; Dec. 1992; pp. 1545–1553.

Letters to the Editor: Journal of Thoracic & Cardiovascular Surgery; "Segmental Tricuspid Annuloplasty: A New Technique"; Jose Revuelta, MD et al; May 1989; pp. 799–801.

Article: "The Surgical Treatment of Mitral Regurgitation"; J. R. Belcher; 1964; pp. 513–523.

Article: "Surgical Treatment of Mitral Systolic Click Syndrome: Results in 37 Patients"; Ian J. Reece, et al.; Feb. 1985; pp. 155–158.

DEVICE FOR TISSUE REPAIR AND METHOD FOR EMPLOYING SAME

BACKGROUND OF THE INVENTION

1. Field of the Invention

The present invention relates to apparatus and methods for repair of weakened tissue in medical and veterinary procedures, such as in weakened heart mitral and tricuspid valve repairs.

2. Description of Related Art

Several accepted procedures exist for reinforcing weakened tissue in medical and veterinary procedures. One area which has received considerable attention in this regard is the repair of mitral and tricuspid heart valves.

As is known, the functioning and effectiveness of human and animal heart valves can be compromised through functional and/or organic causes. If the valve becomes weakened, regurgitation of blood can occur around the valve's leaflets, reducing the heart's effectiveness in pumping blood. While prosthetic devices exist to replace these valves, none is considered fully acceptable. Accordingly, whenever practicable it is accepted practice today to perform conservative surgical procedures to preserve a patient's native valve.

One of the simplest procedures in this regard was developed by Dr. Norberto G. De Vega in the early 1970s ("De Vega"). In this procedure, one or more seams are created within tissue along the periphery of a weakened section of heart valve using conventional suture material. Once the seam is in place, the tissue is simply cinched along the suture in a "purse string" manner. The suture is knotted off at each end, often with the use of pledgets to prevent tearing, to retain the tissue in a plicated orientation. This procedure serves to reduce the size of the valve opening and to improve the valve's efficiency.

Among the advantages of the De Vega procedure are that it is relatively effective at correcting many tricuspid and mitral valve deficiencies, it can be performed rapidly (usually on the order of about 10 minutes), it generally requires little specialized equipment and has a relatively short learning curve, and it generally introduces minimal foreign material within the heart so as to reduce the risk of thrombus generation.

While the De Vega technique has proven to be effective, it continues to be plagued with some serious drawbacks. One serious problem repeatedly observed with the De Vega procedure is that the sutures employed can pull out of the tissue and "guitar string" across the valve annulus. This event not only destroys the repair but also presents an undesirable Obstruction across the valve opening. In one response to this concern, it has been suggested that the sutures should be buried within the atrial endocardium to provide better reinforcement of the suture. Unfortunately this procedure is believed to provide only limited improvement and may result in even more extensive damage in the case of a pull out.

Another suggested correction is the use of pledgets at each stitch in the annulus to reinforce the sutures. While this procedure may solve the tearing problem, it eliminates many of the other advantages of the De Vega procedure, such as the minimizing of foreign material, the speed and ease of the surgery, and the ability to remove the sutures rapidly in the event of the need for further repair or heart valve replacement.

Another common complaint with the De Vega procedure is that the bunching of tissue around the periphery of the valve through the purse string procedure necessarily distorts the valve opening from its natural shape and thus limits improvement in valve function. This problem is particularly compounded where a large segment of the valve is repaired in this manner or where surgeons inexperienced with this technique provide too little or too much plication to the tissue.

Another procedure which has addressed many of the drawbacks of the De Vega technique was developed by Dr. Alain Carpentier in the late 1960s ("Carpentier"). In this procedure a series of different sized fabric coated stainless steel or titanium rings are provided in the approximate original shape of the valves to be repaired. The surgeon first sizes the valve with a sizing template to select the correct size of ring. Next a large number of sutures are sewn in place to create a circle of guide lines around the periphery of the valve annulus. By attaching each of the guide lines to the ring, the ring can be positioned down the guide lines to draw the valve opening into its approximate original shape. Each of the guidelines is then tied off to retain the ring around the annulus.

This technique has been shown to provide significantly improved valve function, but has many critical problems. First, the entire procedure is complicated, requires ancillary equipment, and demands advanced surgical techniques. Moreover, the need to establish and maintain many guide lines through this procedure vastly increases the amount of time needed to perform this repair (generally requiring 30 minutes or more). As a result, due to time constraints it is often impractical to perform a Carpentier repair when this operation is ancillary to other open heart procedures. Other problems with the Carpentier operation include: the risk of off-site impact from the procedure, such as possible surgical damage to the atrioventricular (AV) bundle; the large amount of foreign material exposed to flowing blood, increasing the risk of thrombus generation; and the rigidity of the ring limiting the possible placement and use of this procedure, with particular concern over possibly impeding other heart function, such as distortion of proper systolic motion of the annulus in a mitral valve repair.

The problem of the rigidness of the ring limiting its placement or distorting other heart functions has been addressed through a number of further advances. One device developed by Dr. Carlos M. G. Duran employs a flexible ring, such as one constructed from a flexible polyester polymer, which is mounted in a manner similar to that employed by the Carpentier procedure ("Duran"). Unfortunately, this ring continues to have many of the other drawbacks of the Carpentier ring. Additionally, the flexible ring cannot provide the amount of support possible with a rigid ring, thus decreasing or eliminating one of the chief benefits of the Carpentier device-the restoration and maintenance of the original valve shape.

Another flexible prosthesis is the "flexible linear reducer" developed by Dr. Bex of France. In this device, a silicone bead with embedded polyester fibers is sutured around a distended annulus from one commissure of the affected valve to the other. Unfortunately, this device has many of the same deficiencies as the flexible Duran ring.

Dr. Carpentier has likewise acknowledged some of the deficiencies of his original concept and has developed a number of modifications. Among these are rings which are only semi-rigid, and rings with cut-outs or other modified shapes to avoid affecting other areas of the heart. Again, however, these improved devices still retain many of the same deficiencies discussed above, including excessive installation times and unduly complicated installation procedures.

In light of the foregoing, it is a primary purpose of the present invention to provide an improved apparatus and method of use for reinforcing weakened tissue that can be installed quickly and relatively easily.

It is a further purpose of the present invention to provide such an apparatus and method of use that is resistant to pull-out from anchoring tissue.

It is another purpose of the present invention to provide such an apparatus and method of use that provides an effective repair to cardiac valves by reinforcing the area around the valve's leaflets.

It is still another purpose of the present invention to provide such an apparatus and method that subjects a patient to minimal side effects, such as risk of off-site organ damage or function impediment, or excessively increased risk of thrombosis.

It is yet another purpose of the present invention to provide such an apparatus and method that requires minimal specialized equipment to perform and which can be effectively practiced with a relatively short training curve.

These and other purposes of the present invention will become evident from review of the following specification.

SUMMARY OF THE INVENTION

The present invention is an improved device and method for plicating or cinching tissues together. In one preferred embodiment of the present invention, the device comprises a wide, flexible ligament of expanded polytetrafluoroethylene (PTFE) having at least an end of constricted diameter, and a needle attached to the constricted end of the ligament to permit the ligament to be drawn through an area of tissue to be plicated. The ligament is of sufficient diameter and strength that conventional sutures may be securely anchored within it. Preferably, the ligament comprises a lubricious material that allows the suture needle to pass readily through it and allows tissue to pass readily along the length of the ligament.

In operation, the device of the present invention is inserted through tissue to be plicated in one or more "bites." Once in place, a first end of the ligament is anchored, preferably with the sewing of conventional sutures through the ligament, and the tissue is cinched along the length of the ligament to provide the desired amount of plication. Once the tissue is correctly oriented, the second end of the ligament is then likewise anchored in place, again preferably through the use of a suture sewn through the ligament.

The procedure of the present invention is particularly suitable for use with an annuloplasty operation on mammalian heart valves. The procedure provides a very secure repair of a mitral or tricuspid valve annulus with minimal risk of "guitar string38 pull-out and similar problems encountered with some previous annulus repair techniques. When preferably constructed from a porous polymer, such as porous expanded PTFE, the ligament will experience in-growth within the tissue which provides a long-term repair solution with even further reduced risk of pull-out. The procedure can be performed effectively, rapidly, and with minimal specialized training and equipment. Moreover, the width of the ligament of the present invention avoids the need for extra pledgets or similar reinforcement devices, which can dramatically increase the time and effort needed for installation and removal of some previous annuloplasty devices.

A further improvement of the present invention employs a marker chemical, such as a radio-opaque material which can be observed with x-ray equipment, which allows the ligament to be monitored in situ.

DESCRIPTION OF THE DRAWINGS

The operation of the present invention should become apparent from the following description when considered in conjunction with the accompanying drawings, in which.

DETAILED DESCRIPTION OF THE INVENTION

The present invention is directed to an improved device for plicating tissues.

Figure 1:
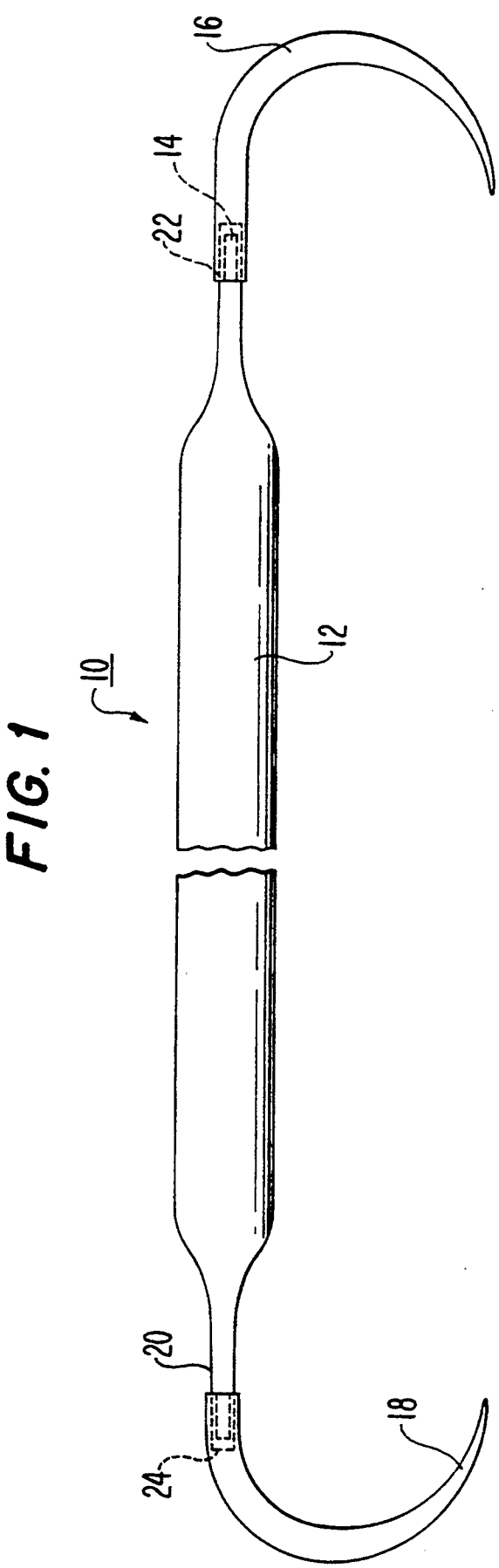
FIG. 1 is a plan view of one embodiment of a tissue repair device of the present invention, including two needles mounted on either end of a truncated ligament.

As is shown in FIG. 1, the device 10 of the present invention comprises a ligament 12 which is attached at one end 14 to a surgical needle 16. For reasons which will become clear from the following description, the ligament 12 employed with the present invention should be sufficiently wide to permit a conventional suture to be readily attached and securely anchored through the ligament intermediate between its ends. Additionally, the ligament material preferably should be sufficiently lubricious to permit a suture needle to pass through it and to allow tissue to move readily along its length.

The basic process of operation of the present invention comprises drawing the device 10 through tissue to form a seam and anchoring the device at a first end by passing a conventional surgical suture through the ligament 12 and tying the ligament in place using the suture. Once one end of the ligament is tied in place, the opposite end of the ligament is grasped and the tissue is moved along the length of the ligament in a "purse string" manner to cinch or "plicate" the tissue into a tightened orientation. The second end of the ligament can then also be tied in place using conventional sutures passing through the ligament.

When installed in this manner, the device of the present invention offers substantial improvements over the use of conventional sutures alone. Most importantly, the device of the present invention provides a sufficiently wide cross-section so that it is highly resistant to being pulled laterally out of attached tissue in normal operation. Additionally, the use of sutures to attach each of the ends of the ligament in place provides a secure anchorage while minimizing the introduction of unnecessary or unnecessarily large foreign objects into a patient's body.

The preferred ligament material comprises a length of polytetrafluoroethylene (PTFE), and particularly porous PTFE, and especially an expanded PTFE. In this instance, the term "porous" is intended to encompass an unfilled PTFE with a bulk density of 2.0 g/cc or less.

The ligament material should have the following specifications: a diameter of about 1.8 mm (within a broad range of 1.0 to 3.0 mm); a length of about 10–20 cm (within a broad range of greater than about 5 cm); an average nodal distance (or "fibril length") in the expanded PTFE matrix of $\geq 18$ microns (within a broad range of greater than 1–5 microns); a peak tensile load of greater than 1.2 kg; and a density of about 0.34 to 0.50 g/cc. Such a product can an be produced in a known manner, such as in accordance with the teachings of U.S. Pat. No. 3,953,566 issued Apr. 27, 1976, to Gore. This material is both highly biocompatible and is quite lubricious, allowing needles and conventional sutures to pass readily through it and permitting tissue to move easily along its length. Similar materials are commercially available in a wide range of various specifications from W. L. Gore & Associates, Inc., Elkton, Md., under the designation GORE-TEX fiber.

The fibril length of porous expanded PTFE that has been expanded in a single direction is defined herein as the average of ten (10) measurements between nodes connected by fibrils in the direction of expansion. The measurements are made in the following manner: First, a photomicrograph is made of a representative portion of the sample surface, of adequate magnification to show at least five sequential fibrils within the length of the photomicrograph. Two parallel lines are drawn across the length of the photomicrograph so as to divide the photograph into three equal areas, with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. The ten measurements obtained by this method are averaged to obtain the fibril length of the material.

Other suitable materials which could be employed with the present invention include: porous polypropylene; porous polyethylene; and porous PET. Additionally, full density material may also be employed with the present invention, either as straight fibers or as braids, but these are not believed to be preferred since ease of needle penetration and/or the degree of ingrowth may be limited with these materials.

Preferably, the ligament material comprises an expanded PTFE material formed as a relatively wide bead with a cross-sectional width of 1.0 to 2.0 mm. In this context, the word "width" refers to the cross-sectional measurement of the bead at its widest segment. The bead may be formed in any suitable cross-sectional shape, including a circle, oval, rectangle, etc. For ease in use and improved reinforcement against tissue, ideally, the ligament material is essentially a cylinder 1.8 mm or wider in cross-section.

As is also shown in FIG. 1, as a further refinement of the present invention a second surgical needle 18 may be attached at the opposite end 20 of the device. As is explained below, when configured in this manner, the device can be installed intermediate to the ends of the tissue to be repaired and tunnelled in opposite directions to accomplish the repair. Alternatively, the opposite end 20 of the device may be left open or, as is explained in greater detail below, may include a pre-installed pledget or other stop device to reduce installation time further.

While the present invention may be employed with virtually any suitably sized needle(s), it is preferred that the needle be of a diameter at its widest section equal to or less than that of the ligament 12 to cause minimal disruption of the tissue in the insertion process. As is shown in FIG. 1, when a needle 16, 18 is provided with a diameter significantly less than that of the ligament 12, the end 14, 20 attached to the needle 16, 18 should be constricted or tapered to provide a smooth transition between the needle and the full width of the ligament 12.

For a ligament with a diameter of approximately 1.8 mm, the preferred needle comprises a diameter of 1.0 mm and an length of 26 mm curved into a ½ or ⅓ circle. Naturally, the precise size and shape of the needle is application specific and may be modified accordingly.

The tapering of the ends of the ligament can be accomplished through any suitable means, including through heating and stretching, densifying, or removing material from the ends, such as through carving, etc. With a ligament 12 of expanded PTFE, the tapering of the ends can be readily accomplished through a heated densification, such as twisting, heating, stretching.

The needles 16, 18 can be attached to the ends 14, 20 through any conventional means. In the embodiment shown in FIG. 1, the needles each include a recessed shank end 22, 24 into which the ligament ends 14, 20 can be inserted and held in place. Retention within the shank ends 22, 24 can be accomplished in any acceptable fashion, including by crimping the shank ends of the needle, or through adhesives (e.g. epoxy or cyanoacrylate) applied to the ligament ends 14, 20.

While the present invention can be employed in a variety of procedures (such as in skin augmentation, for cerclages, and for various organ suspensions), its primary purpose is to serve as an improved mechanism for repairing and reinforcing heart valves. The basic procedure for performing a repair of a tricuspid valve according to the present invention is illustrated in FIGS. 2 through 7.

Figure 2:
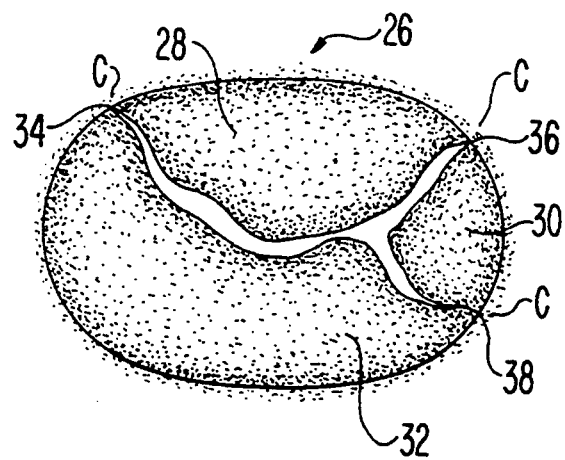
FIG. 2 is a plan view of an enlarged tricuspid valve prior to performing a first embodiment of the procedure of the present invention.
Figure 3:
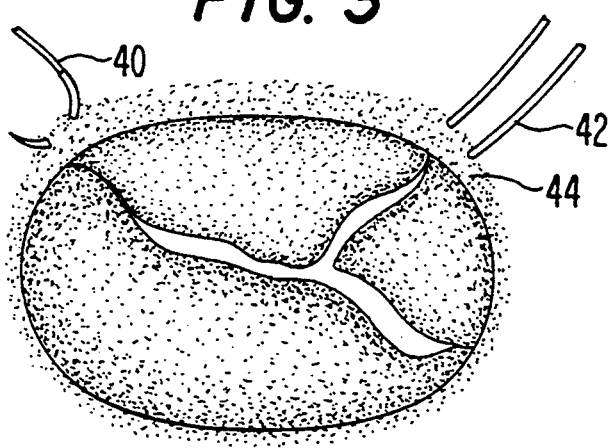
FIG. 3 is a plan view of the tricuspid valve of FIG. 2 with a mattress suture installed at a first commissure and another mattress suture having been installed at a second commissure.
Figure 4:
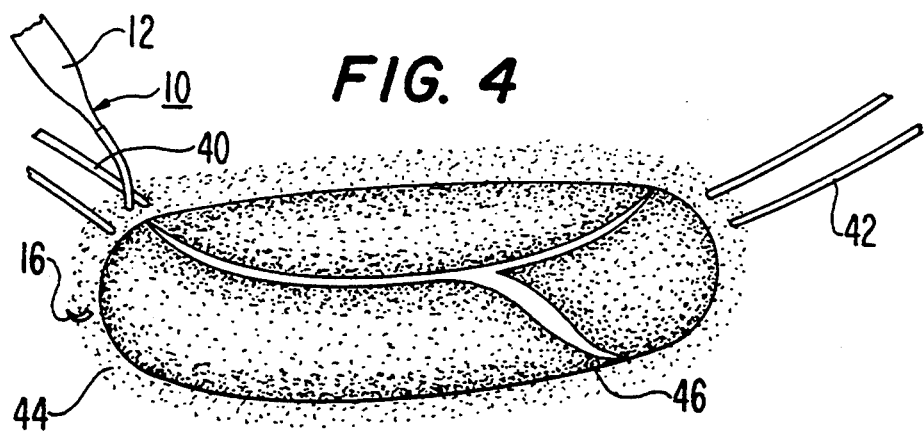
FIG. 4 is a plan view of the tricuspid of FIG. 2 upon initial insertion of the repair apparatus of the present invention.
Figure 5:
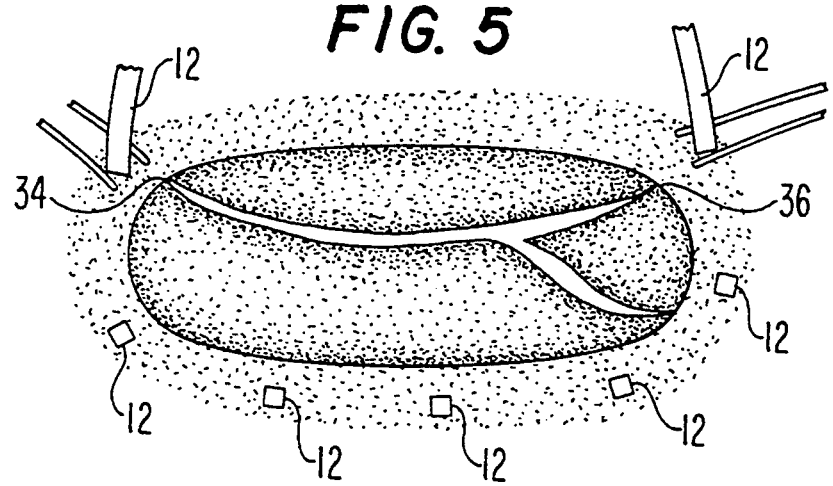
FIG. 5 is a plan view of the tricuspid of FIG. 2 following complete threading of the repair apparatus within the tissue between the first and second commissures.

FIG. 2 shows an enlarged tricuspid valve 26 which is in need of reconstruction. The valve 26 has been exposed through a conventional right atriotomy. The valve comprises three leaflets 28, 30, 32, each connected at commissures 34, 36, 38. To begin the procedure, the two appropriate commissures of the valve are located, the anteroseptal commissure 34 and the posteroseptal commissure 36. As is shown in FIG. 3, mattress sutures 40, 42 are placed in the tissue 44 at these commissures 34, 36 to act as both markers for the device ends and tie-down sutures to hold the device in place. These sutures may include pledgets to protect the tissue from tearing. As is shown in FIG. 4, slight traction on the mattress sutures 40, 42 pulls the anteroposterior annulus 46 into a straighter orientation, to make the process of tunnelling the annuloplasty device 10 of the present invention easier. By inserting needle 16 through tissue 44, the device 10 is tunnelled in several "bites" through the anteroposterior annulus 46, beginning at either the anteroseptal commissure 34 or posteroseptal commissure 36 and ending at the other of the two. After each bite, the flexible ligament 12 of the annuloplasty device is pulled through the annular tissue 44, either with or without counter traction on the tissue. Through this procedure, the ligament 12 is embedded in the tissue and sufficient length is provided for the next bite. Care is taken, both in the tunnelling with the needle 16 and in the pulling of the ligament 12 through the tissue 44, to avoid tearing the annulus. Subsequent bites should begin immediately adjacent to the exit point of the preceding bite in order to maximize the holding power of the tissue and to minimize the amount of ligament exposed to flowing blood. As is shown in FIG. 5, after the ligament 12 is tunnelled all the way through the anteroposterior annulus 46, several centimeters of the flexible member protrude from the area of each of the anteroseptal and posteroseptal commissures 34, 36.

Figure 6:
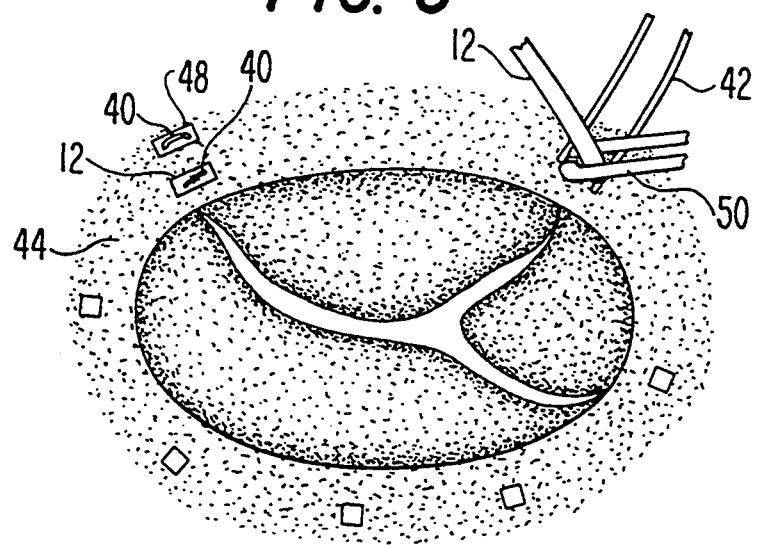
FIG. 6 is a plan view of the tricuspid of FIG. 2 showing the repair apparatus anchored at a first end and being cinched into a repaired position by applying pressure at the second end of the repair apparatus.

As is shown in FIG. 6, at this point, one of the mattress sutures 40 is pierced through the ligament 12 at least once, but as many times as the surgeon chooses, and is tied down to the annular tissue 44. It is preferred that a pledget 48 is employed at this juncture to produce a proper counter force on the opposing side of the tissue 44 to prevent suture tear out. As is shown, the loose ends of the mattress suture 40 may then be cut short.

As was referred to above, a further time saving modification of the present invention can be achieved by pre-installing a pledget or similar stop device on the end of the ligament 12 opposite needle 16. In this manner, the ligament is simply pulled entirely through the annulus in the manner described until the stop is reached. The stop may then be left in this position or be sewn into place for added security.

Figure 7:
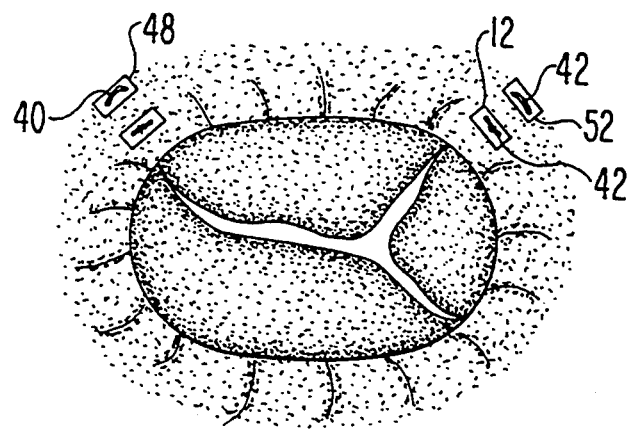
FIG. 7 is a plan view of the tricuspid of FIG. 2 after completion of the repair procedure.

In either instance, next as is shown in FIG. 6, the opposite (i.e. loose) end of the ligament 12 is pulled through the annular tissue 44 while at the same time counter traction is put on the annular tissue 44 in order to "purse string" the annulus and reduce the valve diameter. Pulling of the ligament 12 and counter traction on the tissue can be established by any suitable means, such as through the use of forceps 50. As the length of the anteroposterior annulus is reduced, as is shown in FIG. 7, there is a puckering of the annular tissue, the amount of which is dependent on the amount of shortening of the annulus. Additionally, the portions of the annuloplasty device originally showing between bites tend to disappear in the folds of the annular tissue. The valve can be tested for regurgitation at this point, at the discretion of the surgeon. The counter traction then may or may not be released.

Once a proper valve size has been established, the second mattress suture 42 is attached to the ligament 12 in a manner similar to the first. As is illustrated in FIG. 7, the mattress suture 42 is pierced through the ligament 12 one or more times, near the exit point of the ligament 12 from the tissue tunnel, and tied down to the annulus. A pledget 52 again may be provided to maintain a counter force to prevent tissue tear out. At this stage all traction is released, the mattress suture 42 is cut short and both ends of the ligament 12 are cut short, to within 2–5 mm of the tied down ligament ends. If desired, the valve competence can be tested before cutting the ligament 12, to ensure the proper amount of plication of the annulus.

A modification of this basic procedure is illustrated in FIGS. 8 through 11 in the repair of a mitral valve 54. After normal exposure of the mitral valve 54 by left atriotomy, the two commissures 56, 58 of the valve are located. Pledgeted sutures 60, 62 are placed at the respective commissures 56, 58 to act as both markers for the device ends and tie-down sutures to hold the device in place.

Figure 10:
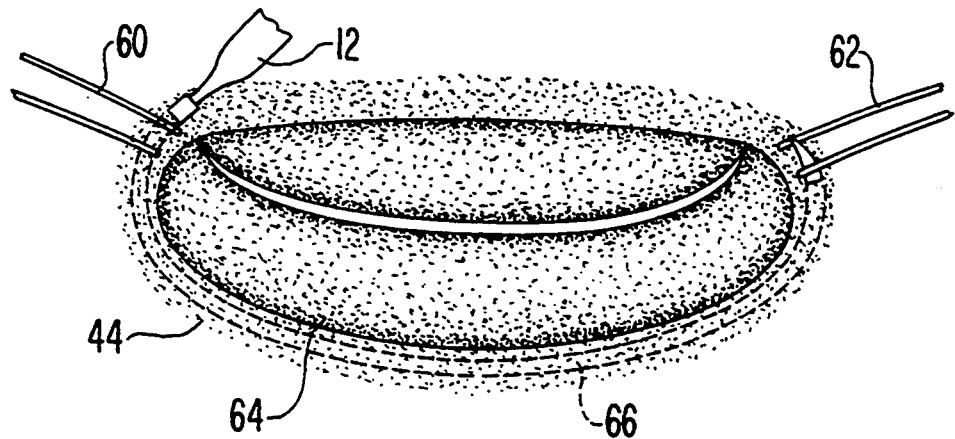
FIG. 10 is a plan view of the mitral valve of FIG. 8 upon insertion of the repair apparatus of the present invention entirely around the weakened valve member between the first commissure and the second commissure.

As is shown in FIG. 10, slight traction on these sutures pulls the posterior annulus 64 into a straighter orientation, to make the process of tunnelling ligament 12 easier.

Instead of tunneling the ligament 12 in a series of small bites as was previously described, an alternative repair can be accomplished by providing a significantly longer needle 66 which can be tunnelled through the repair area in a single bite or in only a couple of large bites. The advantage of this repair is that it maximizes the surface area employed to hold the ligament 12 in place within the tissue 44. Moreover, with the proper sizing of the needle's length and arc, it is believed possible to perform this repair very rapidly, further reducing the overall operation time.

Figure 8:
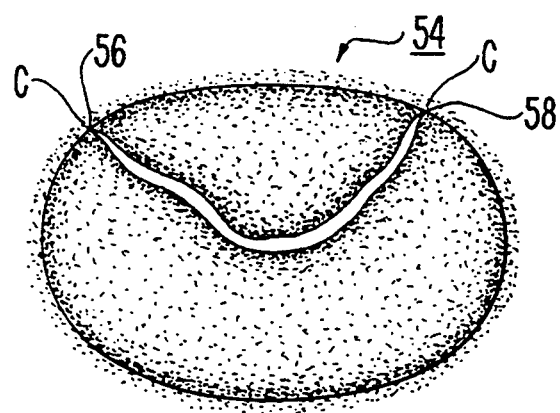
FIG. 8 is a plan view of an enlarged mitral valve prior to performing a second embodiment of the procedure of the present invention.
Figure 9:
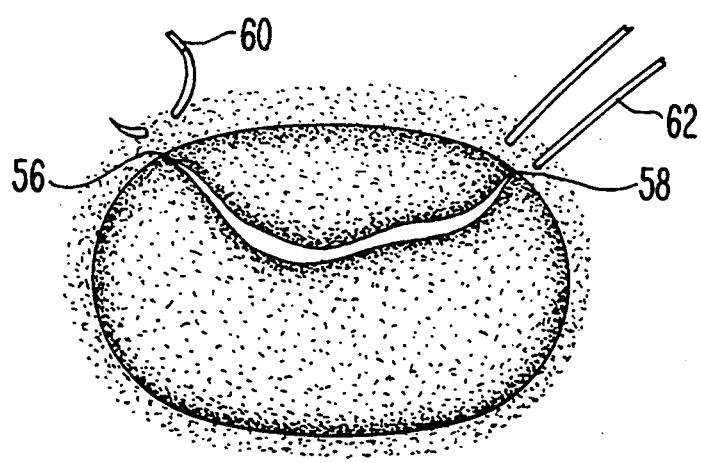
FIG. 9 is a plan view of the mitral valve of FIG. 8 with a mattress suture being installed at a first commissure and another mattress suture having been installed at a second commissure.

The installation of the ligament 12 in a single bite is shown in FIG. 8. The ligament 12 is tunnelled through the posterior annulus of a mitral valve, beginning at one of the commissures 56 and ending at the other commissure 58. Once the needle is properly positioned around the annulus, the ligament 12 is pulled through the annular tissue, either with or without counter traction on the tissue, in order to embed it in the tissue. Care is taken, both in the tunnelling with the needle and in the pulling of the flexible member through the tissue, to avoid tearing the annulus.

Figure 11:
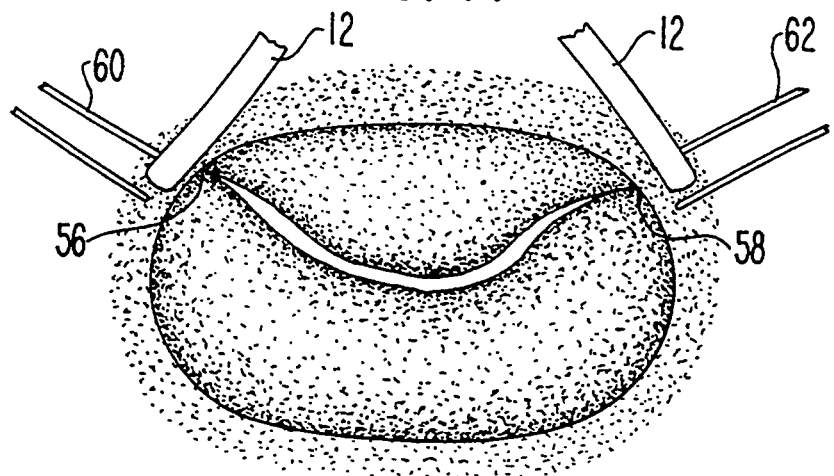
FIG. 11 is a plan view of the mitral valve of FIG. 8 following complete threading of the repair apparatus within the tissue between the first and second commissures.

As is shown in FIG. 11, once the ligament 12 is tunnelled all the way through the posterior annulus 64, a length of several centimeters of the ligament protrudes from the area at each of the commissures 56, 58. At this point, one of the mattress sutures 60 is pierced through the ligament 12 at least once, but as many times as the surgeon chooses, and is tied down to the annular tissue 44 in the manner previously described. Again, a pledget 68 may be used to provide proper counter force on the opposing side of the tissue to prevent suture tear out. Once installed, the loose ends of the mattress suture 60 are cut short. As has been explained, a pledge or other stop device may also be installed at the free end of the ligament to improve the installation speed of this part of the procedure.

Figure 12:
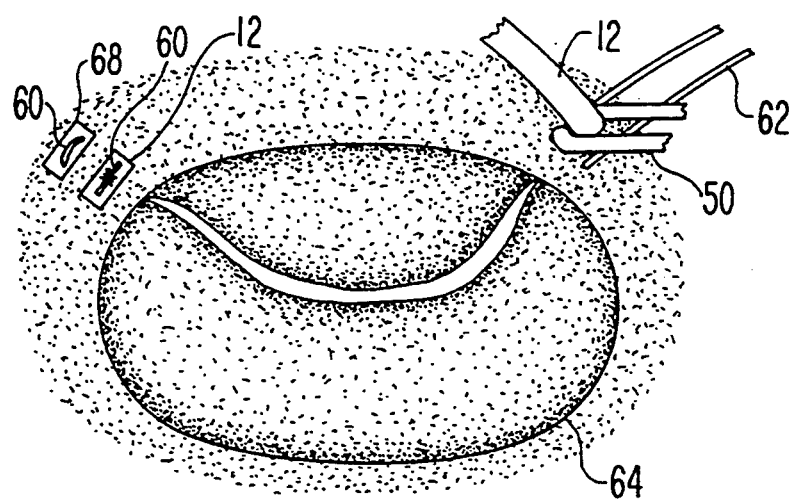
FIG. 12 is a plan view of the mitral valve of FIG. 8 showing the repair apparatus anchored at a first end and being cinched into a repaired position by applying pressure at the second end of the repair apparatus.
Figure 13:
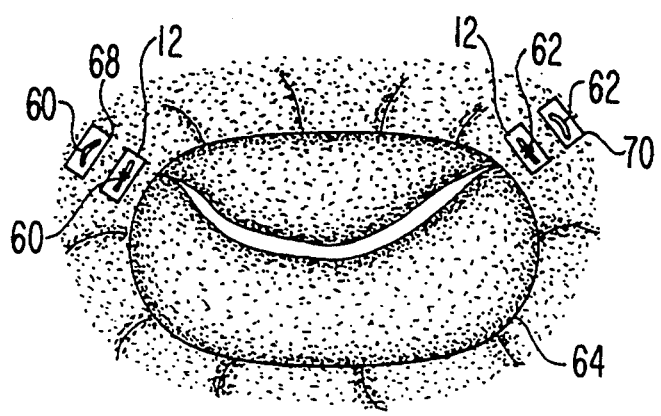
FIG. 13 is a plan view of the mitral valve of FIG. 8 after completion of the repair procedure.

As is shown in FIGS. 12 and 13, next the loose end of the ligament 12 is pulled through the annular tissue while at the same time counter traction is put on the annular tissue with forceps 50 or similar device in order to "purse string" the annulus and reduce the valve diameter. As the length of the posterior annulus is reduced, there is a puckering of the annular tissue, the amount of which is dependent on the amount of shortening of the annulus. The valve can be tested for regurgitation at this point at the discretion of the surgeon. The counter traction then may or may not be released.

To complete the procedure, the second mattress suture 62 is attached to the ligament in a manner similar to the first. It is pierced through the ligament 12 one or more times, near the exit point of the ligament 12 from the tissue tunnel, and tied down to the annulus. A pledget 70 provides counter force to prevent tissue tear out. At this point all traction is released, the mattress suture 62 is cut short, and both ends of the ligament are cut short, to within 2–5 mm of the tied down ligament ends. If ligament, to ensure the proper amount of plication of the annulus.

In addition to possible increase in installation speed, the completely tunneled procedure shown in FIGS. 8 through 13 is believed to present other advantages over the multiple stitch technique shown in FIGS. 2 through 7. For example: the ligament material is exposed only at the ends, thereby reducing the likelihood of embolism formation; and the ligament material exits the tissue only at the ends, so there is a lower possibility of tearing the endothelial layer of the annulus.

Figure 14:
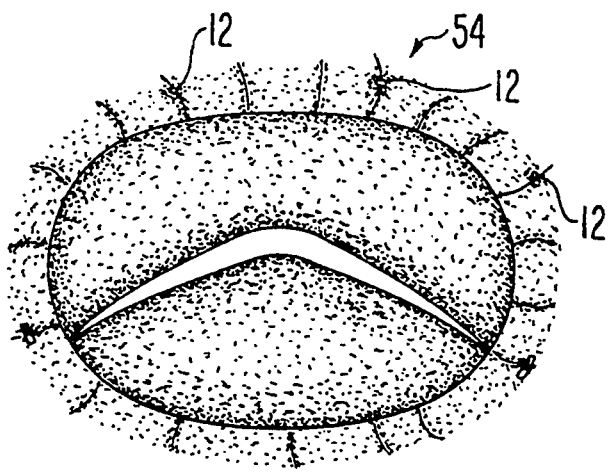
FIG. 14 is a plan view of a mitral valve following performing a procedure similar to that illustrated in FIGS. 2 through 7.
Figure 15:
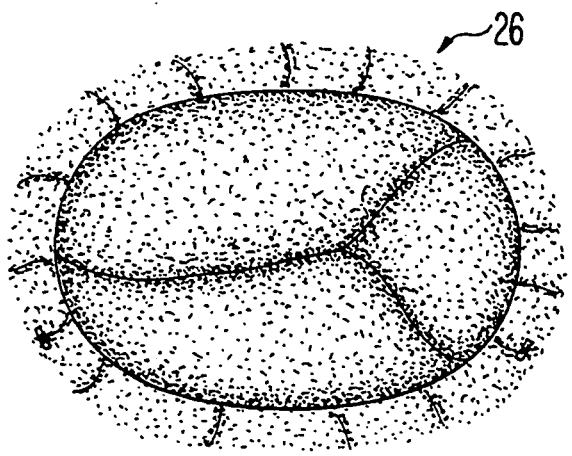
FIG. 15 is a plan view of a tricuspid valve following a procedure similar to that illustrated in FIGS. 8 through 13.

Alternative valve repairs are illustrated in FIGS. 14 and 15. FIG. 14 shows a mitral valve 54 in which a multiple bite repair has been performed. Small portions of the ligament 12 can be seen through the puckered portions of the valve annulus. FIG. 15 shows a tricuspid valve 26 in which a single bite, tunneled repair has been performed.

A summary of various other modified installation techniques of the devices of the present invention are discussed below:

1. Partial plication: In this procedure the ligament is tunnelled in one or more bites from one commissure to some intermediate position on the posterior or anteroposterior annulus between the mitral commissures or the tricuspid anterseptal and posteroseptal commissures, in order to apply plication to only a part of the annulus. Plication may also be between two points intermediate between the appropriate commissures of the valve.
2. Differential plication: The ligament can be tunnelled part of the way around the annulus, and fixed at both tissue tunnel exit points with the correct amount of plication, then tunnelled the rest of the way to the second commissure, plicated a different amount, and fixed at the second commissure. This is to allow different amounts of plication to an annulus that has varying amounts of stretch around its circumference.
3. Complete plication: If the surgeon chooses, he can tunnel the ligament all the way around the annulus, instead of from commissure to commissure, and either suture it to the annulus as described above, or tie it together. This will plicate the annulus evenly all of the way around the valve.
4. Exterior plication: Although significant further study is required in this regard, it is contemplated that a surgeon may be able to run the second, loose end of the ligament through the heart wall to the exterior of the heart, and purse string the valve annulus from the outside. The advantage of this approach would be that the surgeon could monitor the beating heart for regurgitation before plication, then plicate until regurgitation stopped. This would be an exact tailoring of the device for the particular patient and amount of regurgitation.
5. Center outward: As was mentioned previously and is illustrated in FIG. 1, a device 10 may be provided with a needle. 16, 18 at each end of the ligament 12. Using such a double armed device, the surgeon could begin tunnelling in the center of the annulus toward both commissures, moving first toward one commissure with the first needle, and then tunnelling toward the second commissure with the second needle. This approach may provide a distinct advantage where the insertion of the needle from a commissure may be restricted due to space limitations. Space may be a distinct problem when employing an extra large needle such as that shown in FIGS. 8 through
6. More than two anchoring sutures: The surgeon can put a tacking suture at any point where the ligament shows above the tissue. The advantage here is that if the surgeon wants more assurance that the flexible member will stay in its implanted position, he can easily reinforce the ligament along its length with extra sutures but without the need to introduce pledgets or other foreign matter.

As has been mentioned, for greater speed in installation, it may be desirable to provide a pre-installed pledget or other stop device on one end of the ligament to allow it to be rapidly anchored at one end merely by pulling it into place. Two examples of such devices are illustrated in FIGS. 16 and 17.

Figure 16:
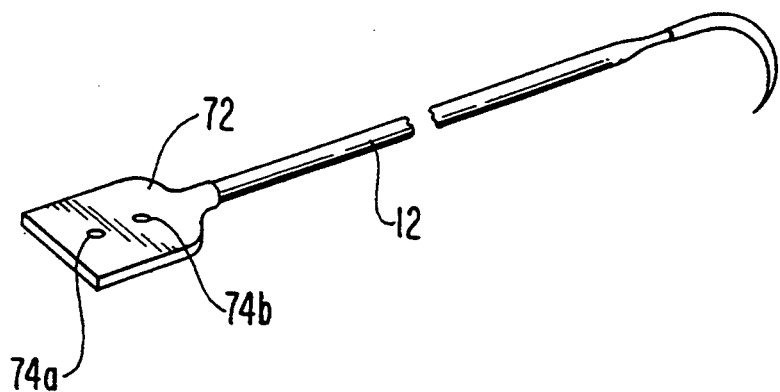
FIG. 16 is a three-quarter perspective view of another embodiment of the tissue repair device of the present invention, including a stop device on one end.

In the embodiment of FIG. 16, the stop device 72 on the end of the ligament 12 comprises an essentially flat pledget. As has been noted, in order to assure greater anchorage it may be desirable to include some means to sew the stop device in place once installed. For example, the stop device 72 may include holes 74a, 74b to receive anchoring sutures and/or may be constructed from a flexible, permeable material that can be sewn into place.

Figure 17:
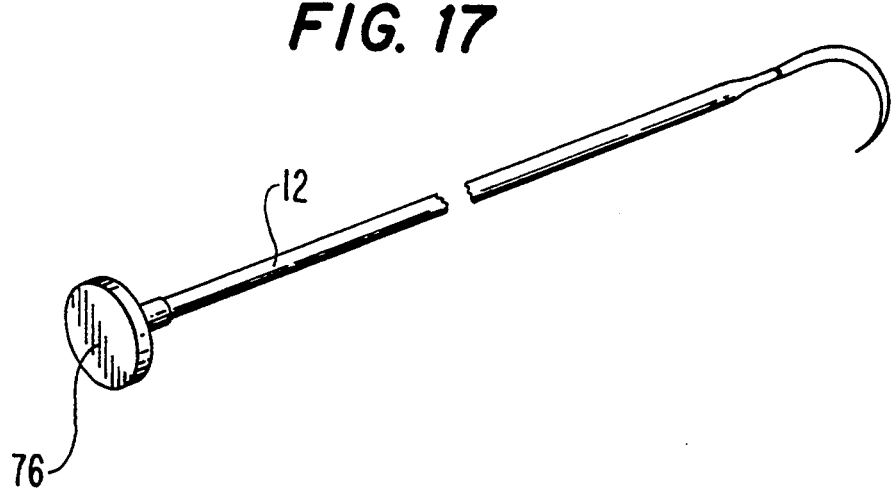
FIG. 17 is a three-quarter perspective view of still another embodiment of the tissue repair device of the present invention, including another embodiment of a stop device on one end.

In the embodiment of FIG. 17, the stop device 76 comprises a disk anchored on the end of the ligament 12. Again, if desired this device may likewise include some form of additional anchoring means to assist in holding it in place.

While the presently preferred embodiments of the present invention are illustrated and discussed above, it should be appreciated that many variations of the present invention are contemplated for specific applications. For instance, for most applications the needle needs to be large enough in diameter to make a tissue tunnel of sufficient size through which to pull the ligament without tearing the annulus. Thus, the thinnest needle would depend on the thinnest ligament which could be used. As presently contemplated, the thinnest ligament which would provide the desired properties of adequate surface area for insertion of a conventional suture, sufficient strength, and sufficient resistance to tear out of the tissue would be about 1 mm in diameter.

The ligament is presently contemplated as being as large as about 3 mm in diameter. Beyond this point, the material is believed to be too bulky to be safely brought through the tissue.

While the ligament of the present invention can be constructed from any suitable material having the properties discussed above, it is preferred that the ligament be constructed from a porous material, such as porous expanded PTFE, to encourage tissue in-growth. For applications where the material is intended to remain permanently in situ once installed, by instituting tissue in-growth a far stronger repair can be provided. To this end, the preferred material comprises an expanded PTFE with an average fibril length (i.e. internodal distance) of greater than or equal to 5 microns.

In addition to ready tissue in-growth, other advantages of employing an expanded PTFE ligament include: high strength and durability; low or nonexistent tissue response; extreme ease in suturing through the expanded PTFE when compared with other suture materials that are full-density; and the ease with which the expanded PTFE ligament will pass through tissue.

The needle design may likewise be widely modified to suit particular needs. For example, the needle may include any suitable point, including a tapered or piercing tip. The needle may be any appropriate length, from as little as about 8 mm. Generally, the needle should be long enough to avoid having to make an excessive number of "bites" in the tissue to which the ligament is attached, which may increase the risk of tearing during the stitching process or during use, or of forming embolus once in place. The needle may be formed with any suitable arc, from a straight needle to a ⅓ or ½ circle or more of any appropriate diameter.

The largest needle is governed by the size of the annulus, the patient size, and the atriotomy size. Generally the needle diameter should not be much larger than that of the ligament since it can create too large a tissue tunnel. To date applicant has experimented with a needle as large as about 7.6 cm long, 2 mm diameter trocar curved into a semicircle for prototype work with 1.8 mm beading.

For a typical application employing a 1.8 mm diameter ligament and a 1.0 mm needle, the length of the densified area from the full-diameter ligament to the needle attachment point should be about at least 1 cm long to provide sufficient length for a smooth transition to full diameter. The advantage of a longer narrow section is that there is less stress on the annular tissue as the ligament is being pulled through the tissue tunnel in the annulus. Then the ligament can be pulled itself, to avoid separating the needle from the ligament.

An important further enhancement of the present invention is providing some form of marker material on or within the ligament to allow the status of the ligament and the repair to be monitored in situ. For example, a radio-opaque material may be embedded within the ligament to distinguish the ligament during x-ray imaging.

The preferred construction in this regard comprises an expanded PTFE ligament material with a filler of barium sulfate, particulate metal (e.g. flaked or powdered metal), metal wire or other embedded radio-opaque strand, or any other suitable radio-opaque material. The radio-opaque material may be installed within the PTFE through any suitable method, such as extruding a preblended material, co-extrusion, pultrusion of a wire, or post infusion. Preferably, the filler is provided by extruding a composite of barium sulfate powder and PTFE powder into a bead shape.

Once such a ligament is constructed, the radio-opaque material can be monitored through use of any conventional x-ray monitoring apparatus. These or other appropriate marker materials may be monitored with echocardiography (i.e. ultrasound monitors) or with magnetic resonance imaging (MRI).

As should be evident from the foregoing description, the device of the present invention provides numerous benefits over previous devices used to plicate tissue. The device can be very rapidly installed yet is highly resistant to pull-out. Moreover, since the device handles in a manner not too dissimilar from conventional sutures, it can be used by surgeons with minimal specialized equipment and training and a vastly reduced learning curve. These attributes provide distinct advantages when the present invention is employed in annuloplasty procedures, providing improved valve performance in a sufficiently short period of time that the procedure of the present invention can be freely performed ancillary to other heart repair procedures.

Without intending to limit the present invention, the following serve as examples of how the device of the present invention may be employed:

EXAMPLE 1

A device was implanted into the right atrioventricular valve of a canine heart. The device consisted of a 1.8 mm diameter bead of expanded PTFE attached to a 7.6 cm long, 2 mm diameter, semicircular needle. The valve was exposed through a right atriotomy and the valve leaflets identified. The device was tunneled from one commissure to the other in one complete bite of the needle. The ePTFE was sutured to the annular tissue near one exit point of the ligament from the annulus using a CV-2 GORE-TEX suture.

Counter traction was applied with the fingers to the annular tissue while the loose end of the device was pulled to cinch the valve to a narrower size. For the purpose of demonstrating the range of plication possible with the present invention, the valve orifice was narrowed to various sizes, down to complete stenosis. At any point of narrowing, releasing all traction on the tissue and device led to the device and tissue remaining at the desired amount of narrowing. At every level of narrowing of the annulus, the annular tissue affected by the device was evenly plicated. The loose end of the device was left loose, to be able to demonstrate the ease and uniformity of plication along the annulus.

This example serves to demonstrate the utility and effectiveness of the single-bite method of implantation, and the evenness of the resulting annular plication over the length of the affected annulus. It also shows the very wide range of variability of annular plication.

EXAMPLE 2

A second device was implanted into a canine right atrioventricular valve. The device consisted, again, of a 7.6 cm long, 2 mm diameter, semicircular needle attached to a 1.8 mm diameter bead of ePTFE. The valve was exposed through a right atriotomy and the valve leaflets identified. The device was tunneled from one commissure to the other in four bites of the needle. The ePTFE was sutured to the annular tissue using a CV-2 GORE-TEX suture near one commissure. Counter traction was applied with the fingers to the annular tissue while the loose end of the device was pulled to cinch the valve to a smaller size. The loose end was then sutured to the annulus near the commissure at which it exited the annular tissue. The valve was plicated to approximately half of its original diameter, with no sign of tear out of either the device or the tie-down sutures from the annulus. The annular tissue along the device was evenly and smoothly plicated.

This example serves to demonstrate the simplicity of implantation, the great extent of annular narrowing available using the method, and the strength of the device when implanted in mammalian tissue.

EXAMPLE 3

A device similar to those described in Examples 1 and 2 above was tunneled part of the way around the right atrioventricular annulus of a canine heart. Approximately 1 cm of the device was tunneled within the annular tissue. The two ends of the device were held in one hand and pulled, while the other hand held the heart steady. The pull severely distorted the shape of the annulus, but did not tear out of or show signs of tearing the annulus.

COUNTER EXAMPLE 3a

A CV-0 GORE-TEX suture was tunneled part way around the atrioventricular annulus of a canine heart. This suture, with a diameter of approximately 0.9 mm, is one of the widest conventional sutures commonly available. Approximately 1 cm of the suture was tunneled within the annular tissue. The two ends of the suture were held in one hand and pulled, while the other hand held the heart steady. The suture easily pulled laterally out of the annular tissue, creating a tear as long as the tunneled length of suture.

Example 3 and Counter Example 3a serve to further demonstrate the strength of the large-diameter ligament as used in this application, and the failure in strength of the largest suture normally used in cardiac procedures.

EXAMPLE 4

A device similar to that in Examples 1 to 3 was implanted into a live canine heart in the left atrioventricular position. The dog was anesthetized under normal procedures, and the heart exposed by medial sternotomy. After placing the cardiovascular system on complete cardiopulmonary bypass, the left atrioventricular valve was exposed by a left atriotomy. The anterior and posterior commissures of the valve were located and marked with CV-2 GORE-TEX sutures, pledgeted and mattressed. The device was tunneled from the posterior to the anterior commissure in one bite of the needle, so that the complete posterior annulus contained the flexible ligament tunneled within it, and with no visible portions except at the exit points near the commissures.

Next, the flexible ligament was sutured to the annulus using the marking suture at the posterior commissure. The suture, double armed, was drawn through the flexible ligament twice-once with each needle—and secured to the annulus with multiple suture knots. The loose end of the device was pulled while counter traction to the annular tissue was provided in order to purse-string the annulus to shorten it. The annulus was cinched to approximately ⅓ its normal size, and the loose end of the flexible ligament fastened with the other marking suture in the same manner as the first suture—both needles of the suture were passed through the flexible ligament, and the suture knotted several times to hold the end firmly to the annular tissue. The completed procedure narrowed the mitral orifice evenly and effectively. At this point, the dog was sacrificed and the heart autopsied to show that there was no damage to collateral structures in the heart. This example demonstrates the effectiveness of the single-bite/large-needle annuloplasty with the device of the present invention. It also shows the utility of this device in a real surgical setting, and that no collateral damage is caused to nearby cardiac structures as a result of the device and procedure.

EXAMPLES 5

For this example, devices were made with 1.8 mm diameter expanded PTFE beading attached to semicircular suture needles. The needles were 26 mm long, 0.98 mm in diameter at their widest point, and contained a taper point. One of these devices was implanted into the left atrioventricular valve position of a canine heart. The valve was exposed with a left atriotomy and the commissures identified with pledgeted, mattressed, CV-2 GORE-TEX sutures. The device was tunneled in a series of bites from the posterior commissure to the anterior commissure. After each bite, a length of flexible ligament was pulled through the tissue tunnel formed by the needle. Each successive bite after the first was started near to the exit point of the previous bite. A total of 5 bites was made to encircle the valve from one commissure to the other along the posterior annulus. The end of the device at the posterior commissure was fastened to the annular tissue by piercing both needles of the suture marking that commissure through the flexible ligament and securely tying it down. The loose end of the device was pulled through the tissue as counter traction was applied to the tissue with forceps, to purse-string the annulus to a small diameter. A firm pull on the device caused a complete stenosis of the valve, and the valve remained that way even when all traction was released from both the device and the tissue. A finger inserted into the valve served to reopen the valve to the desired diameter. The second suture was fastened to the device at its commissure in the same manner as the first suture, in order to hold the plicated annulus in place. The sutures and the ligament ends were cut short. This test required approximately 7 minutes to complete.

This example serves to demonstrate that the device can be implanted in a series of short bites of the needle through the annular tissue and that it retains the characteristics of simplicity of procedure, speed, ease of adjustment, and strength as demonstrated in earlier examples. Further, it shows that the device can be made with needles significantly smaller in diameter than the flexible ligament itself and not tear the tissue in implantation.

EXAMPLE 6

Another device as described in Example 5 was implanted into the right atrioventricular valve position of the same heart as was used in Example 5. In this instance, the specific device was double armed, i.e. had needles attached at both ends of the flexible ligament. The valve was exposed via right atriotomy and the two commissures identified with pledgeted, mattressed, CV-2 GORE-TEX sutures. The device was implanted by tunneling one needle from the center of the free-wall (non-septal) annulus to a commissure in two bites of the needle, and tunneling the other end in a like manner but in the opposite direction to the other commissure. One end was sutured as in previous examples to the annular tissue, and the tissue was then cinched to narrow the valve opening. Finally, the other suture was set at the other end of the flexible ligament to hold the annular tissue in place, and both sutures and ends of the ligament were trimmed short.

This example demonstrates that a double armed device can be implanted from the center of the annulus of a right atrioventricular valve to the two commissures such that the plication of the tissue is equivalent to that of implantation from one commissure to the other. It further shows that more than one device can be implanted into a single heart without them interfering with each other. Finally, it demonstrates that a single type of device can be implanted into both the right heart and left heart positions without adjusting the technique for size or adjusting the device for shape or size.

EXAMPLE 7

The device described in Example 5 was implanted into a live canine heart for examination in an acute survival setting. A 48 lb greyhound was anesthetized and the heart exposed through a medial sternotomy. The dog was placed on complete cardiopulmonary bypass and the heart arrested. The left atrioventricular valve was exposed through a left atriotomy and the valve commissures identified with pledgeted, mattressed, CV-2 GORE- TEX sutures. Slight traction on the commissural sutures pulled the posterior annulus into a straight line. The device was tunneled in several bites from the posterior to the anterior commissure as described in Example 5, and the end of the device at the posterior commissure sutured down to the annular tissue as described in previous examples. The loose end of the device was pulled while at the same time counter traction was put onto the annular tissue with forceps, in order to cinch the annulus to about ⅓ of its original diameter. Traction was removed and the second suture used to hold the device in place, as described in earlier examples. The sutures and ends of the device were cut short. The whole annuloplasty procedure lasted approximately 5.5 minutes.

The heart was then closed and restarted with normal blood flow. The heart was allowed to beat freely under the influence of isoproterenol hydrochloride, in order to simulate a strongly beating heart, for 15 minutes. The subject was then sacrificed and the heart autopsied. The device remained in place under the stress of normal heartbeats and blood pressure with no dehiscence or suture detachment.

This example serves to demonstrate that the device is effective in maintaining a narrowed valve orifice under the influence of a strongly beating heart, in the more stressed of the two positions (left position). It also reconfirms the speed with which the device can be implanted in a surgical setting.

COUNTER EXAMPLE 7a

For this example, a device was made with a 1.8 mm diameter expanded PTFE beading attached to a 26 mm long semicircular needle. The needle had a taper point and a maximum diameter of 0.62 mm. A 62 lb greyhound was anesthetized and the heart exposed by a right lateral thoracotomy. The dog was placed on complete cardiopulmonary bypass and the heart arrested. The left atrioventricular valve was exposed via a left atriotomy, and the valve commissures identified with pledgeted, mattressed, CV-2 GORE-TEX sutures. Slight traction on the sutures pulled the posterior annulus into a straight line. The device needle was tunneled from the posterior commissure in its first bite, and an attempt was made to pull the flexible ligament through the tissue tunnel left by the needle. However, the annular tissue tore in this process, beginning at the needle end of the device, moving toward the full-diameter end of the device.

This counter example serves to demonstrate that the correct combination of flexible ligament diameter and needle diameter must be chosen in order to obtain sufficient ease of implantation and at the same time to prevent damaging the annular tissue during the implantation.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A method for plicating tissue which comprises:
    providing a repair device which comprises a ligament of sufficient cross-sectional width to permit the attachment and secure retention of a suture within the ligament, and, attached to at least one end of the ligament, a needle adapted to be inserted into and out of the tissue along a length of the tissue to be plicated;
    installing the repair device along the length of the tissue;
    anchoring the ligament at one end of the length of tissue;
    applying pressure at the opposite end of the length of tissue to cause the tissue to plicate along the ligament;
    attaching a suture through the ligament to the outside of the plicated portion of tissue to assist in retaining the tissue in a plicated orientation.

2. The method of claim 1 which further comprises providing a ligament of sufficient cross-sectional width to avoid tearing of the tissue during use.

3. The method of claim 1 which further comprises providing a ligament with a cross-sectional width of at least 1 mm at its widest portion.

4. The method of claim 1 which further comprises attaching sutures to the ligament on either side of the plicated length of tissue.

5. The method of claim 1 which further comprises employing the repair device in a heart to provide reinforcement of a heart valve.

6. The method of claim 1 which further comprises inserting the needle and ligament into and out of the tissue multiple times over the length of tissue to be repaired.

7. The method of claim 1 which further comprises inserting the needle and ligament into and out of the tissue only once on either side of the length of tissue to be repaired.

8. The method of claim 1 which further comprises
providing a ligament of a porous polymer with sufficiently open structure so as to permit tissue in-growth therein; and
embedding the ligament at least partially within the tissue so as to promote tissue in-growth within the ligament.

9. The method of claim 1 which further comprises
providing a marker material within the ligament which can be perceived by monitoring apparatus; and
observing the repair device once installed through use of the monitoring apparatus.

10. A method for creating an annuloplasty which comprises:
providing a repair device which comprises a ligament of sufficient cross-sectional width that it resists tearing through tissue, and a needle attached to one end of the ligament;
inserting the needle at least once into and out of a repair site of a valve annulus;
pulling the needle and ligament through the repair site;
anchoring the ligament at one end;
cinching the tissue in the repair site along the ligament to form a plicated section;
attaching a suture through the ligament to assist in retaining the tissue in a plicated state on the ligament.

11. The method of claim 10 which further comprises providing a needle on each end of the ligament;
attaching the ligament through the repair site by drawing each of the needles into and out of the tissue.

12. The method of claim 10 which further comprises
providing a ligament with a widest cross-sectional width of at least 1 mm; and
attaching to the ligament a needle with a cross-sectional width less than that of the ligament, the end of the ligament attached to the needle being tapered to form a smooth transition between the needle and the ligament.

13. The method of claim 10 which further comprises retaining the tissue in a plicated orientation on the ligament by attaching sutures to the ligament on both sides of the plicated tissue.

14. The method of claim 10 which further comprises
providing a marker within the ligament to allow it to be viewed by monitoring apparatus; and
monitoring the status of the annuloplasty once installed by viewing the ligament's marker through use of the monitoring apparatus.

* * * * *